United States Patent
Rossi (10) Patent No.: US 6,953,459 B2
(45) Date of Patent: Oct. 11, 2005

(54) ICE DISPENSER FOR COLD THERAPY

(76) Inventor: Geoffrey A. Rossi, 4046 36th Ave. West, Seattle, WA (US) 98199

( * ) Notice: Subject to any disclaimer, the term of this patent is extended or adjusted under 35 U.S.C. 154(b) by 148 days.

(21) Appl. No.: 10/437,793

(22) Filed: May 12, 2003

(65) Prior Publication Data

US 2004/0230266 A1 Nov. 18, 2004

(51) Int. Cl.[7] .............................................. A61B 18/18
(52) U.S. Cl. ........................... 606/20; 606/23; 424/439; 426/100
(58) Field of Search ............................... 606/20, 22–23; 607/96, 104, 105; 426/100, 112; 424/439

(56) References Cited

U.S. PATENT DOCUMENTS

| | | | | |
|---|---|---|---|---|
| 3,417,862 A | * | 12/1968 | Fong | 206/517 |
| 3,595,449 A | * | 7/1971 | Stump et al. | 222/386 |
| 5,111,973 A | * | 5/1992 | Mueller | 222/386 |
| 5,693,077 A | * | 12/1997 | Friedman | 607/96 |
| 6,231,904 B1 | * | 5/2001 | Mueller | 426/112 |

* cited by examiner

Primary Examiner—Roy D. Gibson
(74) Attorney, Agent, or Firm—Michael J. Bolan (57) ABSTRACT

This invention relates to the field of medical instruments and particularly to an apparatus used to apply cryotherapy to an injury. The apparatus is comprised of a vessel, a driver, and a directional controller. The vessel is configured such that when it is filled with a liquid and refrigerated, the resultant frozen solid formed within the vessel can be extruded via an exiting aperture. The driver forms a watertight seal with the vessel, allowing the vessel to be filled with liquid and frozen. The directional controller comprises flexible tabs that exert pressure on the sides of the frozen solid, limiting the movement of the frozen solid to one-way extrusion. The user applies force to the driver, thereby urging the frozen solid past the directional controller and out via the exit aperture.

40 Claims, 8 Drawing Sheets

ICE DISPENSER FOR COLD THERAPY

CROSS-REFERENCE TO RELATED APPLICATIONS

Not Applicable

STATEMENT REGARDING FEDERALLY SPONSORED RESEARCH OR DEVELOPMENT

Not Applicable

DESCRIPTION OF THE ATTACHED APPENDIX

Not Applicable

BACKGROUND OF THE INVENTION

1. Field of Invention

This invention relates generally to the field of medical instruments and more specifically to an ice dispenser for the application of cryotherapy or ice massage therapy to an injury.

2. Prior Art

The application of ice or other cold materials to an injury, known as cryotherapy, has long been used as an effective treatment for burns, bruises, arthritic joints and a variety of musculo-skeletal injuries, including sprains, strains, and fractures. It has also been found to be useful in the rehabilitation process after minor surgery, such as arthroscopic surgery. Generally, the goals of cryotherapy are to limit the formation of edema, to reduce pain, and to reduce muscle spasms. There are various types of devices, systems, and methods used today to apply cryotherapy including ice massage, ice immersion, cold whirlpools, ice bags, cold gel packs, cold chemical packs, and vapor-coolant sprays. In the past, ice massage was commonly applied with a piece of ice made by freezing a disposable paper or plastic cup filled with water. This method had several disadvantages. It was awkward and ineffective in that the user's hand was subjected to the low temperature of the frozen liquid. The heat of the user's hand also contributed to premature melting of the ice, thus lessening the useful life of the ice for treatment. Further, it was difficult to control the ice massage to the wounded area, since the cup began to collapse as the ice inside melted, offering a poor gripping surface. Furthermore, the ice would easily slip out of the cup and fall, becoming soiled and difficult to pick up and place back in the cup. Another method was to hold the piece of ice in a cloth. While initially helping to insulate the user's hand from the ice, the cloth quickly became wet from the melting ice, and the wet cloth would again transmit the cold to the user's hand. The use of a piece of cloth also made it difficult to control the pressure and location of the ice massage as it afforded an imprecise and loose grip on the ice.

An ice applicator for medicinal purposes by Hanson, et al. (U.S. Pat. No. 4,537,194 Aug. 27, 1985) uses a cup filled with water and a lid with an open top that engages the water when placed on the cup. When the cup and lid assembly are refrigerated, the resultant ice inside the cup forms with a mechanical attachment to the lid. The lid is then removed from the cup, pulling the ice with it, and acting as a handle for the ice.

A ball of ice gel by Bontemps (U.S. Pat. No. 5,127,395 Jul. 7, 1992) uses a hollow polyolefin sphere containing a frozen cooling mixture that is maintained at a temperature of about—20.degree C. The filled sphere functions to accumulate negative kilocalories and is manipulated by means of an isothermal plastic handle or sleeve in order to apply the sphere to the epidermis.

A treatment of vascular and tension headache, atypical facial pain, and cervical muscle hyperactivity by Friedman (U.S. Pat. No. 5,676,691 Oct. 14, 1997) uses plastic tubes encasing a column of ice, which ice can be extruded gradually by the patient or clinician by means of a plunger inserted into the tubes to apply ice to the area of tenderness associated with the plexus formed by the posterior superior alveolar branch of the ipsilateral maxillary nerve, as well as to other branches of the trigeminal nerve. Immediately preceding the application of the cold, an injection of a conventional dental anesthetic in the conventional amount used for that purpose could be made.

OBJECTS AND ADVANTAGES

The primary object of the invention is to provide an apparatus and method for making, storing, dispensing, and applying a frozen solid to an injured area.

Another object of the invention is to provide an apparatus and method for making, storing and applying a medicated frozen solid to an injured area.

Another object of the invention is to provide an apparatus and method for applying cold therapy, known as cryotherapy to an injured area.

A further object of the invention is to provide an apparatus that allows the frozen solid to be exposed incrementally as required, keeping the remainder of the frozen solid from melting.

Yet another object of the invention is to provide an apparatus that allows the frozen solid to be applied with pressure as required to provide ice massage while keeping the frozen solid from pushing back into the apparatus.

Still yet another object of the invention is to provide an apparatus that allows the application of cryotherapy without transmitting cold to the hand that is holding the apparatus.

Another object of the invention is to provide an apparatus that is shaped so as to be comfortable to hold, manipulate and control while providing a secure grip to the user.

Another object of the invention is to provide an apparatus that allows simple and effective breaking of the adhesion between the frozen solid and the vessel with one hand.

Another object of the invention is to provide an apparatus that allows partial use of the frozen solid, with the ability to be re-filled and frozen without removing the unused portion of the frozen solid.

A further object of the invention is to provide an apparatus that acts as a watertight container, thus preventing leakage and/or spilling if the frozen solid should melt while the apparatus is stored or transported.

Yet another object of the invention is to provide an apparatus and method for keeping the frozen solid insulated from melting for an extended period of time, thus allowing for the transportation and storage of the apparatus until needed.

A further object of the invention is to provide an apparatus and method for keeping the frozen solid refrigerated for an extended period of time, thus allowing for the transportation and storage of the apparatus until needed.

Still yet another object of the invention is to provide an apparatus and method for storing and transporting multiple units of frozen solid for an extended period of time that is both leak-proof and insulated.

Yet another object of the invention is to provide an apparatus and method for keeping multiple units of frozen solid refrigerated for an extended period of time, thus allowing for the transportation and storage of the apparatus until needed.

Other objects and advantages of the present invention will become apparent from the following descriptions, taken in connection with the accompanying drawings, wherein, by way of illustration and example, an embodiment of the present invention is disclosed.

BRIEF SUMMARY OF THE INVENTION

The apparatus is comprised of a vessel, a driver, and a directional controller. The vessel is configured such that when it is filled with a liquid and refrigerated, the resultant frozen solid formed within the vessel can be extruded there from. The driver forms a watertight seal with the vessel, allowing the vessel to be filled with liquid and frozen. The user applies force to the driver, thereby dispensing the frozen solid from the vessel. The directional controller limits the movement of the frozen solid to one-way extrusion.

In accordance with a preferred embodiment of the invention, there is disclosed a machine or apparatus for the making, storing and application of cryotherapy or ice massage therapy comprising:

(a) a vessel with at least one exiting aperture configured such that when the vessel is filled with a liquid and refrigerated, the resultant frozen solid formed within the vessel can be extruded via the exiting aperture (b) a driver for urging the frozen solid from the exiting aperture of the vessel (c) a directional controller for limiting the travel of the frozen solid to one-way extrusion through the exiting aperture in the vessel In accordance with a preferred embodiment of the invention, there is disclosed a machine or apparatus for the making, storing and application of cryotherapy or ice massage therapy comprising:

(a) a vessel with at least one exiting aperture configured such that when the vessel is filled with a liquid and refrigerated, the resultant frozen solid formed within the vessel can be extruded via the exiting aperture (b) driver means for urging the frozen solid from the exiting aperture of the vessel (c) controlling means for limiting the travel of the frozen solid to one-way extrusion through the exiting aperture in the vessel In accordance with a preferred embodiment of the invention, there is disclosed a method for the making, storing and application of cryotherapy or ice massage therapy comprising the steps of:

(a) providing a vessel filled with a frozen solid, and (b) extruding the frozen solid from the vessel to incrementally dispense the frozen solid, and (c) applying the frozen solid to tissues in need of treatment, whereby the application melts the frozen solid against the tissues in need of treatment to cool the tissues

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

Figures.

REFERENCE NUMERALS

10 Vessel
11 Frozen Solid
12 Directional controller
14 Locking Means
16 First Gripping Surface
18 Second Gripping Surface
19 Access Aperture
20 Driver
21 Void
22 Sealing Surface
24 Driver Base
26 Retainer
30 Sealing Closure
32 Bearing Surface
34 Sealing Surface
40 Water-Tight Vessel Assembly
50 Insulated Storage Means
52 Bearing Lip
54 Depression
56 Cavity
60 Insulated Storage Means
62a Depression
62b Depression
66a Closure Means
66b Closure Means
68 Hinge
69 Cavity
80 Insulated Base
82 Depression
84a Closure Means
84b Closure Means
86 Cavity
88 Insulated Lid
90 Insulated Storage Means
110 Insulated Storage Means
112a Depression
112b Depression
116a Closure Means
116b Closure Means
118 Hinge
119 Canity

DETAILED DESCRIPTION OF THE PREFERRED EMBODIMENTS

Detailed descriptions of the preferred embodiment are provided herein. It is to be understood, however, that the present invention may be embodied in various forms.

Therefore, specific details disclosed herein are not to be interpreted as limiting, but rather as a basis for the claims and as a representative basis for teaching one skilled in the art to employ the present invention in virtually any appropriately detailed system, structure or manner. The invention is described below with the aid of FIGS. 1–8. It should be understood that FIGS. 1–8 represent only an exemplary embodiment of an ice applicator system according to the invention. An ice applicator system in accordance with the invention may be embodied in many variations that do not depart essentially from the embodiments described herein. It should be further understood that FIGS. 1–8 are only schematic depictions of ice applicator systems in accordance with the invention, and these figures do not limit the scope of the invention, which is defined by the claims below.

The present invention comprises an inexpensive, safe, simple machine or apparatus by which ice or some other frozen substance for cryotherapy or ice massage can be made, stored, and applied to burns, arthritic joints or sports-related injuries in a safe, clean, comfortable, efficient and convenient manner and without discomfort to the person applying the treatment. The device is comprised of a vessel, a driver, and a directional controller. The vessel is configured such that when it is filled with a liquid and refrigerated, the resultant frozen solid formed within the vessel can be extruded via an exiting aperture. The driver forms a watertight seal with the vessel, allowing the vessel to be filled with liquid and frozen. The directional controller comprises flexible tabs that exert pressure on the sides of the frozen solid, limiting the movement of the frozen solid to one-way extrusion. The user applies force to the driver, thereby urging the frozen solid past the directional controller and out via the exit aperture.

Figure 1:
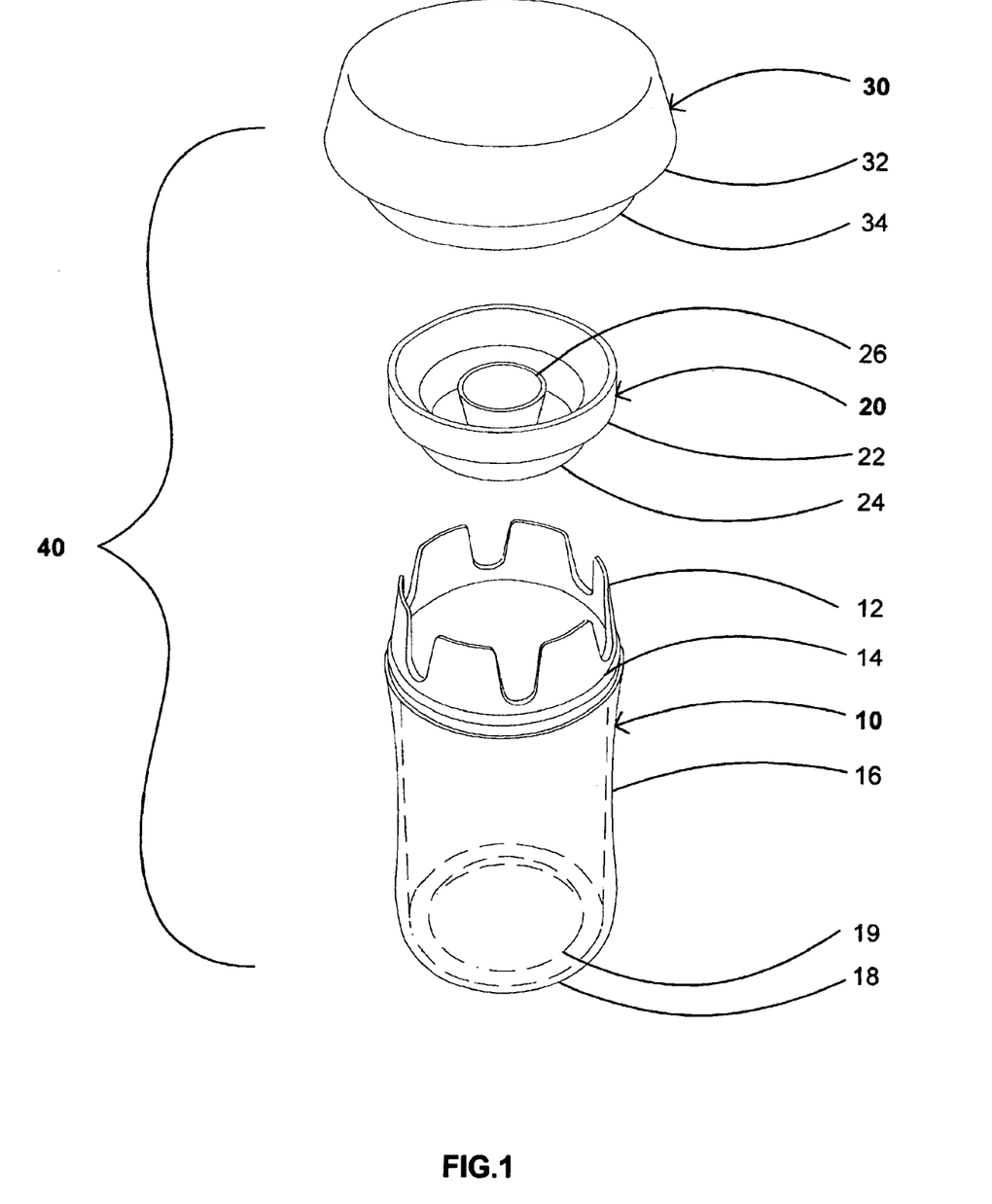
FIG. 1 is an exploded view of the invention.
Figure 4:
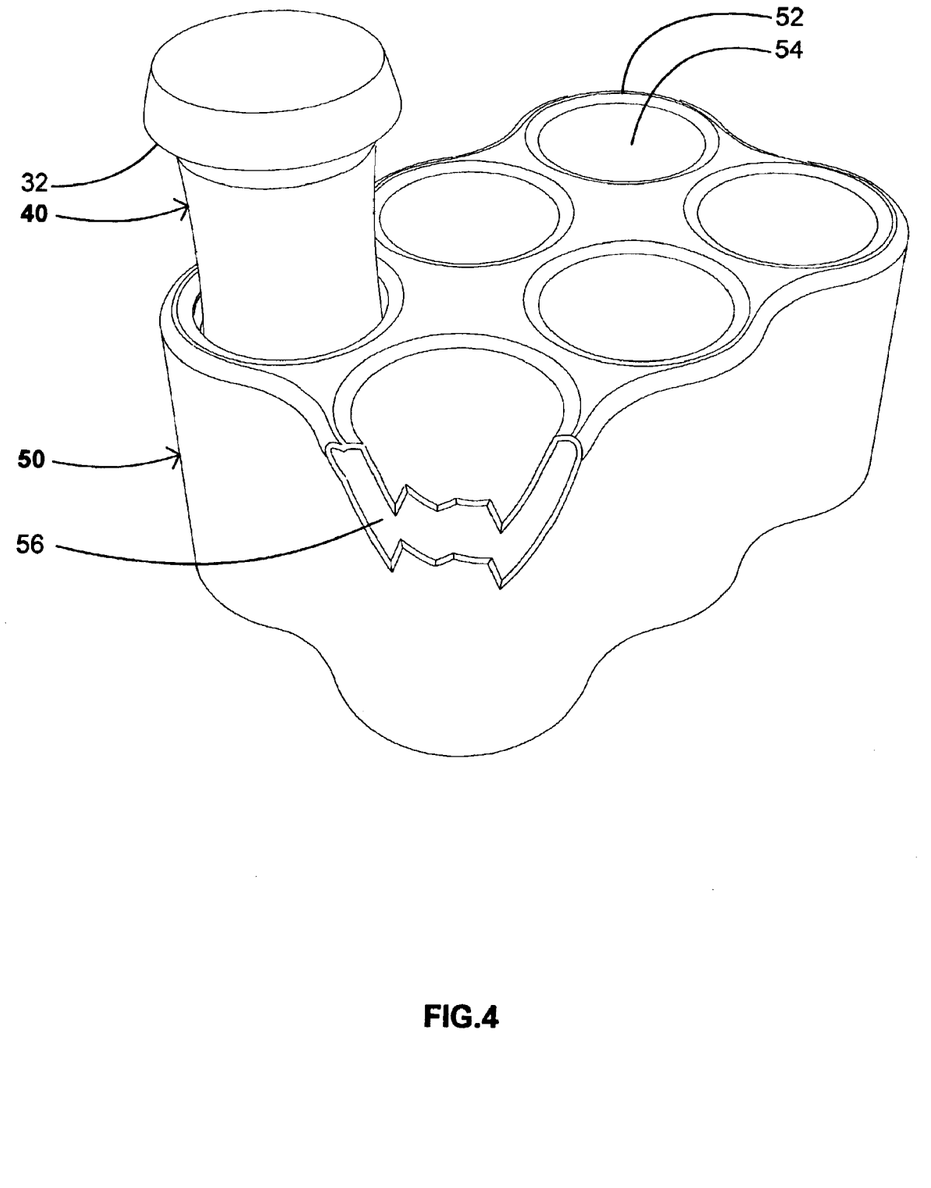
FIG. 4 is a partially cross-sectional perspective view of the invention.

Referring now to FIG. 1 of the drawings, an apparatus according to the invention is shown to comprise a vessel 10, a directional controller 12 and a driver 20. In the preferred embodiment, vessel 10 is configured with a first gripping surface 16 shaped to afford a firm grip while the user is in the process of removing sealing closure 30 or applying force to driver 20 through aperture 19 to urge the frozen solid from vessel 10. Driver 20 is shown configured with a sealing surface 24 which forms a water-tight seal with vessel 10, allowing vessel 10 to be filled with a liquid and refrigerated to form a frozen solid. Driver 20 is also shown configured with a base portion that can protrude through aperture 19 of vessel 10 when driver 20 is in its lowest position relative to vessel 10. The user may strike or push this protruding base portion of driver 20 against a surface to break the adhesion between the frozen solid and vessel 10, initiating the dispensing of the frozen solid from vessel 10. Those skilled in the art will recognize that both driver 20 and vessel 10 could be configured in a wide variety of shapes and could be constructed from many different materials and still perform as required. Since ice massage is often performed with pressure applied to the tissues in need of treatment, the user may place the applicator in the palm of the hand, using second gripping surface 18, which is shaped with a beveled surface to afford a comfortable grip while the user is applying the frozen solid to the injured tissues. In the preferred embodiment, driver 20 comprises a retainer 26 to allow the frozen solid to form with a mechanical attachment to driver 20. Those skilled in the art will recognize that retainer 26 could be configured in a wide variety of shapes and could be constructed from many different materials and still perform as required. Sealing closure 30 is shown comprising a sealing surface 34 configured to form a watertight seal with vessel 10, while being held securely in place by locking means 14 on vessel 10. Sealing closure 30 is also shown configured with a bearing surface 32, which could be used to suspend the device in a depression within an insulated storage means as shown in FIG. 4. With sealing closure 30 held securely in place via locking means 14, the components vessel 10, driver 20 and sealing closure 30, form watertight vessel assembly 40

Figure 2:
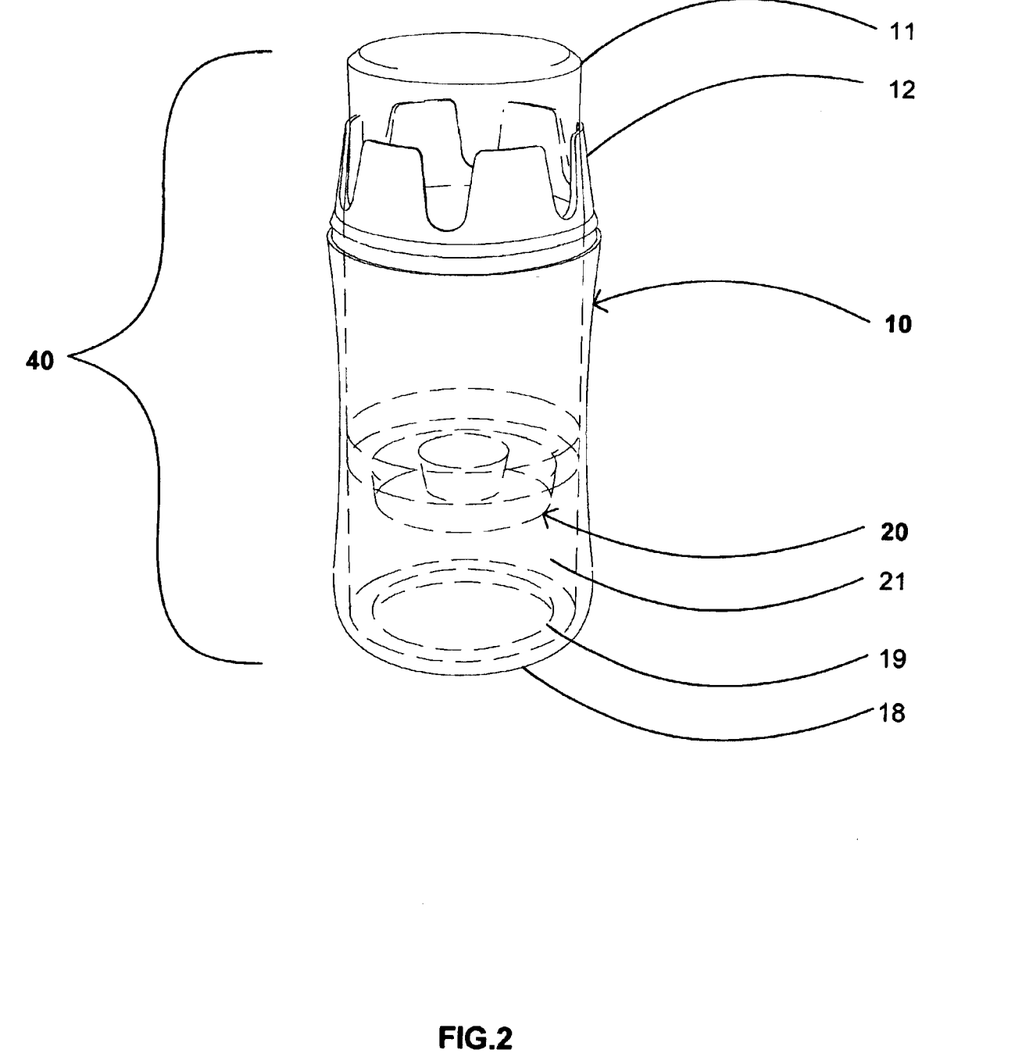
FIG. 2 is a perspective view of the invention when assembled.

In FIG. 2 of the drawings, the preferred embodiment of the device is shown ready for use with frozen solid 11 partially extruded from vessel 10. Directional controller 12 exerts pressure on the sides of frozen solid 11, limiting the travel of frozen solid 11 to one-way extrusion. As the user applies force to driver 20 through access aperture 19 in vessel 10 to urge frozen solid 11 out of vessel 10 past directional controller 12, a void 21 is created behind driver 20. This void 21 allows the user to grasp the device in the palm of the hand by second gripping surface 18 such that the user's hand is insulated from the cold of frozen solid 11.

Figure 3:
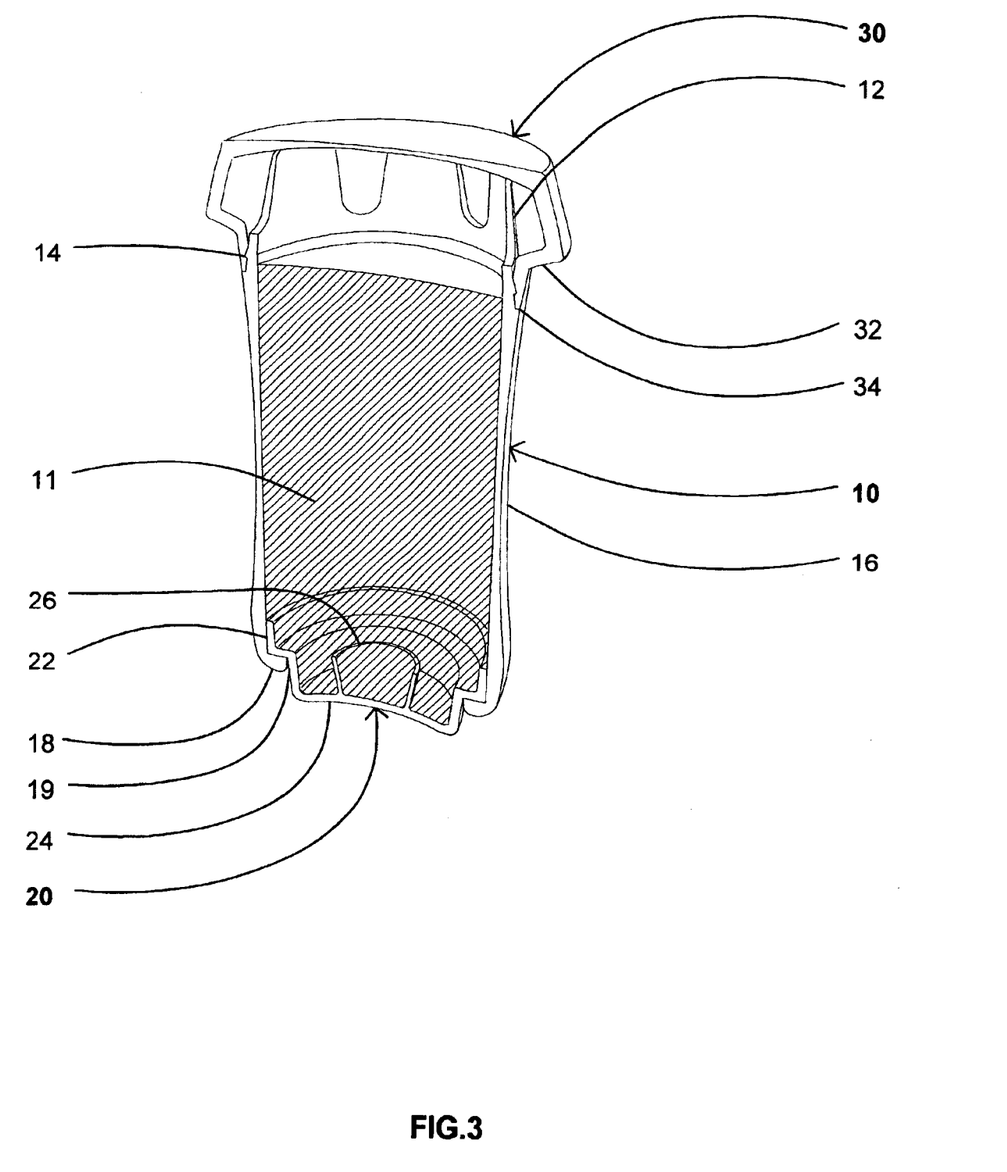
FIG. 3 is a partially cross-sectional perspective view of the invention.

FIG. 3 shows a partially cross-sectional perspective view to illustrate the relationship of the components of the device in its preferred embodiment. FIG. 3 clearly illustrates the manner in which driver base 24 protrudes from aperture 19 of vessel 10, allowing the user to strike or push this protruding base portion of driver 20 against a surface to break the adhesion between frozen solid 11 and vessel 10, initiating the dispensing of the frozen solid from vessel 10. FIG. 3 also clearly shows the beveled shape of second gripping surface 18, which would afford a comfortable grip while the user grasps the device in the palm of the hand at gripping surface 18 and applies frozen solid 11 to the injured tissues. With sealing closure 30 held securely in place via locking means 14, the components vessel 10, driver 20 and sealing closure 30, form a water-tight vessel assembly 40

FIG. 4 shows an alternate embodiment of the invention, including insulated storage means 50 which would be used to keep the frozen solid contained in a plurality of watertight vessel assemblies 40 from melting for an extended period of time, allowing for transportation or storage of the frozen solid until needed. FIG. 4 shows watertight vessel assembly 40 placed in a depression 54 of insulated storage means 50 such that bearing surface of watertight vessel assembly 40 rests against bearing lip 52 of insulated storage means 50. Insulated storage means 50 is shown configured with a double-walled construction, thereby forming cavity 56 which can be filled with a number of insulating materials including, but not limited to insulating foam or dead air space. In an alternate embodiment, cavity 56 can be filled with a re-freezable material to provide a portable means for keeping the watertight vessel assemblies 40 refrigerated for an extended period of time.

Figure 5:
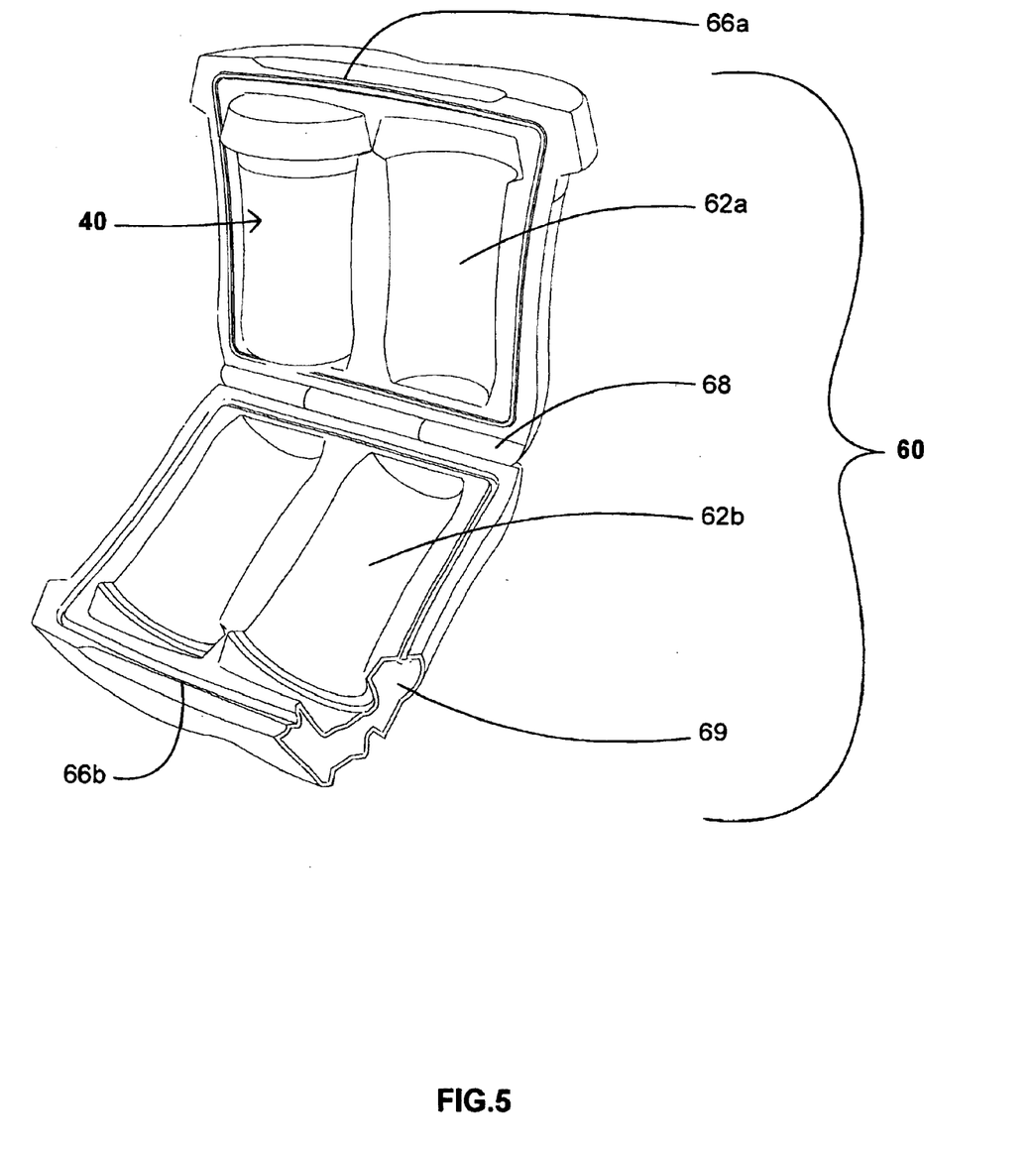
FIG. 5 is a partially cross-sectional perspective view of the invention.

FIG. 5 shows another embodiment of the invention, including insulated storage means 60 which would be used to keep the frozen solid contained in a plurality of watertight vessel assemblies 40 from melting for an extended period of time, allowing for transportation or storage of the frozen solid until needed. FIG. 5 illustrates a clamshell design of insulated storage means 60 with two matching halves that are connected via hinge 68 and held closed via closure means 66a and 66b. Watertight vessel assembly 40 may be contained securely in depressions 62a and 62b of insulated storage means 60 when insulated storage means 60 is held closed by closure means 66a and 66b. Insulated storage means 60 is shown configured with a double-walled construction, thereby forming cavity 69 which can be filled with a number of insulating materials including, but not limited to insulating foam or dead air space. In an alternate embodiment, cavity 69 can be filled with a re-freezable material to provide a portable means for keeping the watertight vessel assemblies 40 refrigerated for an extended period of time.

Figure 6:
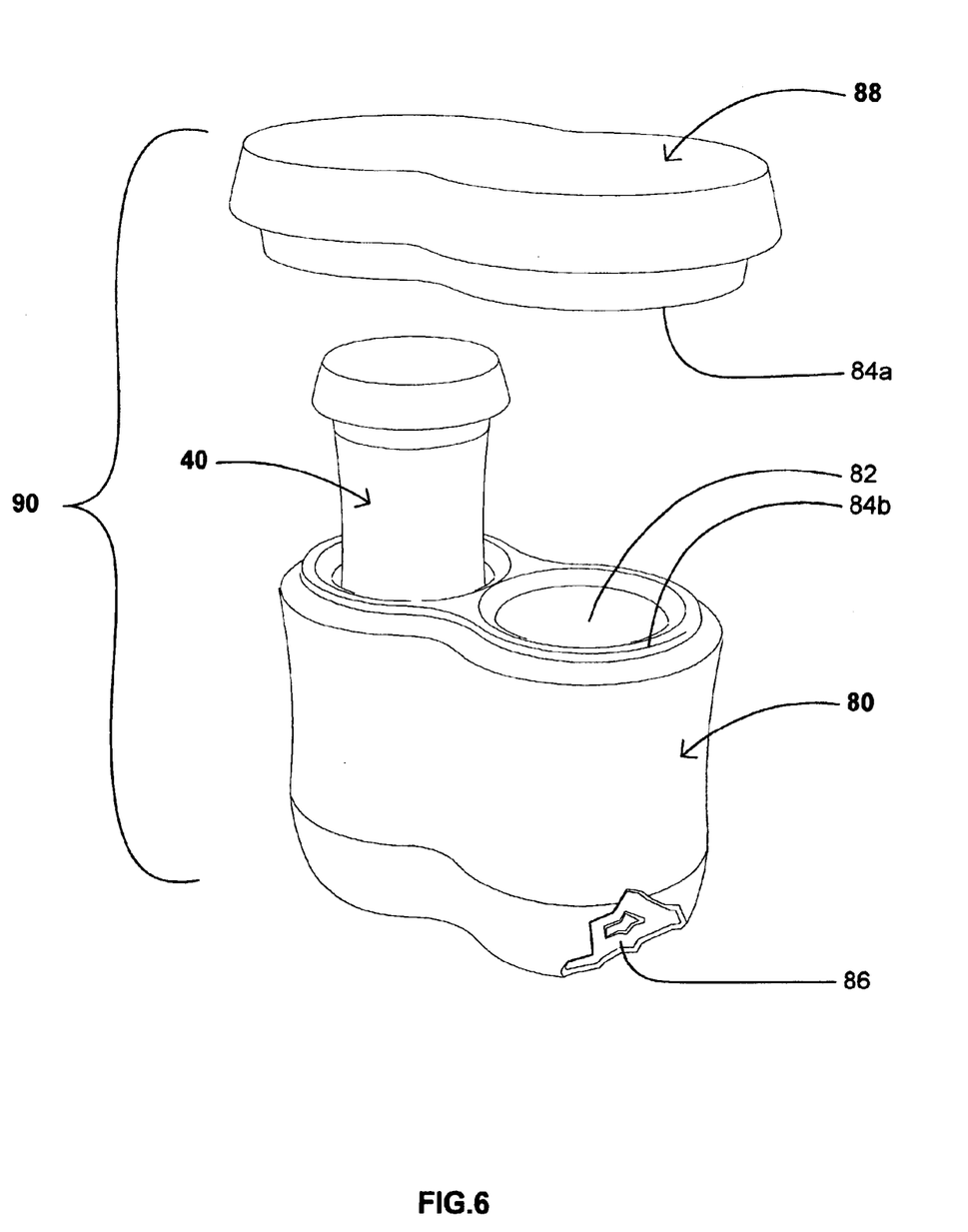
FIG. 6 is a partially cross-sectional perspective view of the invention.

FIG. 6 shows another embodiment of the invention, including insulated storage means 90 which would be used to keep the frozen solid contained in a plurality of watertight vessel assemblies 40 from melting for an extended period of time, allowing for transportation or storage of the frozen solid until needed. FIG. 6 illustrates a drop-in design of insulated storage means 90 with depressions configured to receive a plurality of watertight vessel assemblies 40. Insulated lid 88 is held securely to insulated base 80 via closure means 84*a* and 84*b*.

Insulated storage means 90 is shown configured with a double-walled construction, thereby forming cavity 86 which can be filled with a number of insulating materials including, but not limited to insulating foam or dead air space. In an alternate embodiment, cavity 86 can be filled with a re-freezable material to provide a portable means for keeping the watertight vessel assemblies 40 refrigerated for an extended period of time.

Figure 7:
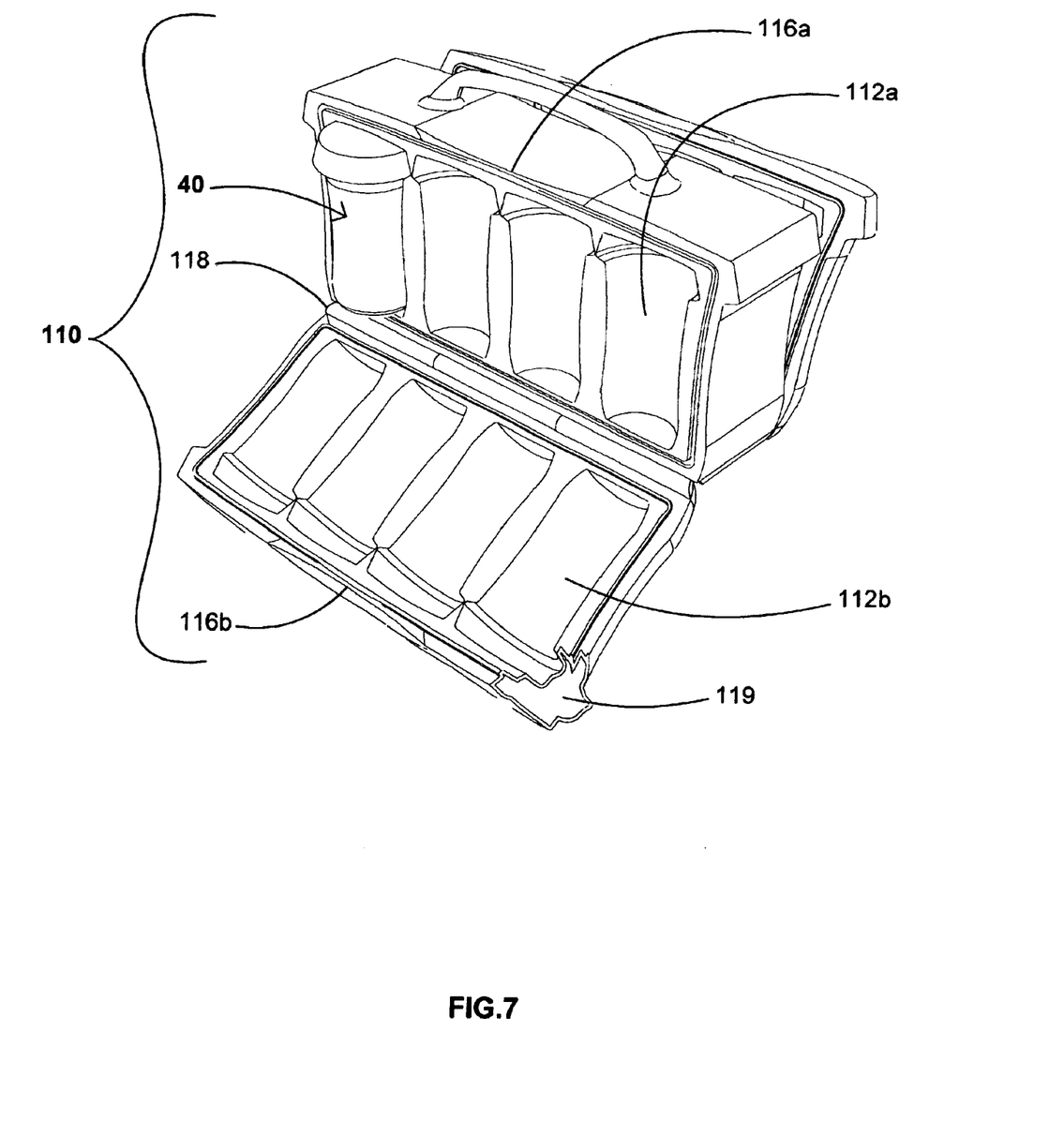
FIG. 7 is a partially cross-sectional perspective view of the invention.
Figure 8:
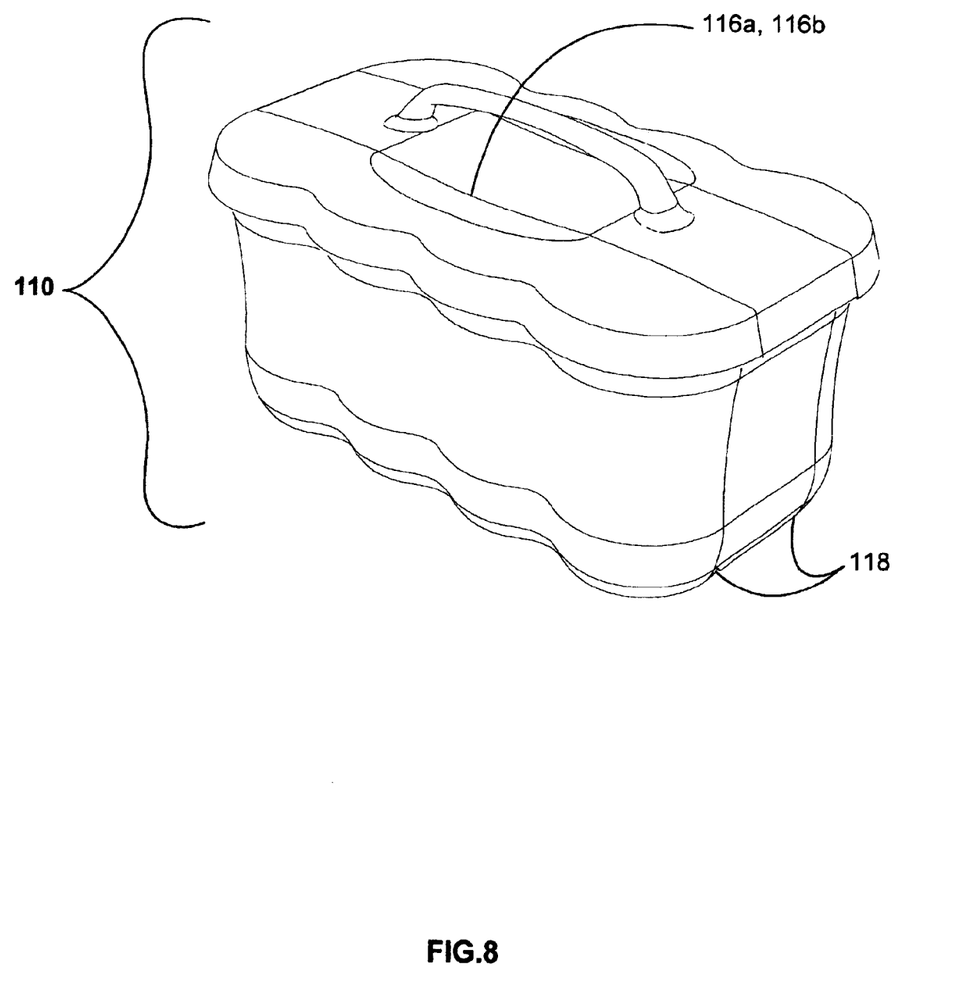
FIG. 8 is a partially cross-sectional perspective view of the invention.

FIG. 7 and FIG. 8 show yet another embodiment of the invention, including insulated storage means 110 which would be used to keep the frozen solid contained in a plurality of water-tight vessel assemblies 40 from melting for an extended period of time, allowing for transportation or storage of the frozen solid until needed. FIG. 7 illustrates a double clamshell design of insulated storage means 110 with two matching halves that are connected via hinges 118 to a double sided core 114 and held closed via closure means 116*a* and 116*b*. Watertight vessel assemblies 40 may be contained securely in depressions 112*a* and 112*b* of insulated storage means 110 when insulated storage means 110 is held closed by closure means 116*a* and 116*b*. Insulated storage means 110 is shown configured with a double-walled construction, thereby forming cavity 119 which can be filled with a number of insulating materials including, but not limited to insulating foam or dead air space. In an alternate embodiment, cavity 119 can be filled with a re-freezable material to provide a portable means for keeping the watertight vessel assemblies 40 refrigerated for an extended period of time.

Numerous characteristics and advantages of the invention have been set forth in the foregoing description, together with details of structure and function of the invention, and novel features thereof are pointed out in the appended claims. The disclosure, however, is illustrative only, and changes may be made in detail, especially in matters of shape, size and arrangements of parts, within the principle of the invention, to the full extent indicated by the broad, general meaning of the terms in which the appended claims are expressed.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. An apparatus for the application of cryotherapy or ice massage therapy, comprising:
   (a) a vessel with at least one exiting aperture configured such that when said vessel is filled with a liquid and refrigerated, the resultant frozen solid formed within said vessel can be extruded via said at least one exiting aperture;
   (b) a driver for extruding the frozen solid from said at least one exiting aperture; and
   (c) a directional controller for directly engaging the frozen solid to limit the extruded frozen vessel from moving back into said at least one existing aperture.

2. An apparatus according to claim 1, wherein said vessel is constructed of an insulating material.

3. An apparatus according to claim 1, wherein said driver is configured to form a water-tight seal with the inside of said vessel to allow said vessel to be filled with a liquid, refrigerated, and frozen until needed.

4. An apparatus according to claim 1, wherein said driver is configured to protrude from an access aperture in said vessel, thereby allowing the user to strike or push the protruding portion of said driver against a surface to break the adhesion between the frozen solid and the vessel, thereby initiating the extrusion of the frozen solid there from.

5. An apparatus according to claim 1, wherein said driver comprises a retainer configured to allow the frozen solid to mechanically attach to the driver.

6. An apparatus according to claim 1, wherein the outer surface of said vessel comprises features to help the user maintain a firm grip on the vessel.

7. An apparatus according to claim 1, further comprising a closure forming a watertight seal with said vessel at said at least one exiting aperture.

8. An apparatus according to claim 1, wherein said directional controller is configured to directly engage the frozen solid to limit the travel of the frozen solid to one-way extrusion through said at least one exiting aperture.

9. An apparatus according to claim 1, wherein said directional controller is directly affixed to said vessel.

10. An apparatus for the application of cryotherapy or ice massage therapy, comprising:
    (a) a vessel with at least one exiting aperture configured such that when said vessel is filled with a liquid and refrigerated, the resultant frozen solid formed within said vessel can be extruded via said at least one exiting aperture;
    (b) driver means for urging the frozen solid from the exiting aperture of said vessel; and
    (c) controlling means for limiting the travel of the frozen solid to one-way extrusion through said at least one exiting aperture.

11. An apparatus according to claim 10, wherein said vessel is constructed of an insulating material.

12. An apparatus according to claim 10, wherein said driver means is configured to form a water-tight seal with the inside of said vessel to allow said vessel to be filled with a liquid, refrigerated, and frozen until needed.

13. An apparatus according to claim 10, wherein said driver means is configured to protrude from an access aperture in said vessel, thereby allowing the user to strike or push the protruding portion of said driver means against a surface to break the adhesion between the frozen solid and the vessel, thereby initiating the extrusion of the frozen solid there from.

14. An apparatus according to claim 10, wherein said driver means is configured with a retainer means configured to allow the frozen solid to mechanically attach to the driver means.

15. An apparatus according to claim 10, wherein the outer surface of said vessel comprises features to help the user maintain a firm grip on the vessel.

16. An apparatus according to claim 10, further comprising a closure means forming a watertight seal with said at said at least one exiting aperture.

17. A method for the application of therapy comprising:
(a) providing a vessel filled with a frozen solid;
(b) extruding said frozen solid from said vessel incrementally to dispense said frozen solid; and
(c) applying said frozen solid to tissues in need of treatment, whereby the application melts the frozen solid against the tissues in need of treatment to cool said tissues, wherein the travel of the frozen solid is limited to one-way extrusion by exerting pressure on the sides of the frozen solid without applying substantial pressure to the exterior of the vessel.

18. A method according to claim 17, further comprising limiting the extruded frozen solid from moving back into said vessel.

19. A method according to claim 17, further comprising insulating said frozen solid within said vessel.

20. A method according to claim 17, further comprising storing said vessel filled with frozen solid within an insulated storage device.

21. A method according to claim 17, further comprising storing a plurality of said vessels filled with frozen solids within an insulated storage device.

22. A method according to claim 17, further comprising sealing said vessel.

23. The method of claim 17, wherein the cooling of the tissue provides therapy to the tissue.

24. The method of claim 17, wherein the travel of the frozen solid is limited by the operation of a directional controller.

25. An apparatus for the application of cryotherapy or ice massage therapy, comprising:
(a) a vessel with at least one exiting aperture configured such that when said vessel is filled with a liquid and refrigerated, the resultant frozen solid formed within said vessel can be extruded via said at least one exiting aperture;
(b) a driver for urging the frozen solid from said at least one exiting aperture of said vessel; and
(c) flexible tabs configured to apply pressure to the sides of the extruded frozen solid, thereby limiting the travel of the frozen solid to incremental, one-way extrusion through said at least one exiting aperture.

26. An apparatus according to claim 25, wherein said vessel is constructed of an insulating material.

27. An apparatus according to claim 25, wherein said driver is configured to form a water-tight seal with the inside of said vessel to allow said vessel to be filled with a liquid, refrigerated, and frozen until needed.

28. An apparatus according to claim 25, wherein said driver is configured to protrude from an access aperture in said vessel, thereby allowing the user to strike or push the protruding portion of said driver against a surface to break the adhesion between the frozen solid and the vessel, thereby initiating the extrusion of the frozen solid there from.

29. An apparatus according to claim 25, wherein said driver comprises a retainer configured to allow the frozen solid to mechanically attach to the driver.

30. An apparatus according to claim 25, wherein the outer surface of said vessel comprises features to help the user maintain a firm grip on the vessel.

31. An apparatus according to claim 25, further comprising a closure forming a watertight seal with said vessel at said at least one exiting aperture.

32. An apparatus according to claim 25, wherein said flexible tabs are affixed to said vessel.

33. An apparatus for the application of cryotherapy or ice massage therapy, comprising:
(a) a vessel with at least one exiting aperture configured such that when said vessel is filled with a liquid and refrigerated, the resultant frozen solid formed within said vessel can be extruded via said at least one exiting aperture;
(b) a driver for urging the frozen solid from said at least one exiting aperture of said vessel;
(c) a directional controller for limiting the travel of the frozen solid to one-way extrusion through said at least one exiting aperture; and
(d) an insulated storage device with a depression that conforms to and receives said vessel.

34. An apparatus according to claim 33, wherein said storage device has a plurality of depressions that conform to and receive a plurality of said vessels.

35. An apparatus according to claim 33, wherein said vessel has a bearing surface for suspending said vessel in said depression.

36. An apparatus according to claim 33, wherein said storage device comprises a cavity filled with a freezable liquid or gel.

37. An apparatus according to claim 33, wherein said storage device comprises a cavity filled with an insulating material.

38. An apparatus according to claim 33, wherein said depression is a drop-in depression.

39. An apparatus according to claim 33, wherein said storage device comprises two halves with matching depression portions that form the depression when the two halves are closed.

40. An apparatus according to claim 33, wherein said storage device comprises a core having two opposing sides with two respective depression portions, a first half with a depression portion that forms one depression with one of said two opposing depression portions when said first halve is closed against one of said core sides, and a second halve with a depression portion that forms another depression with the other of said two opposing depression portions when said second halve is closed against the other of said core sides.

* * * * *